Dec. 9, 1969 M. L. MEILLAND Plant Pat. 2,949
ROSE PLANT
Filed March 18, 1968
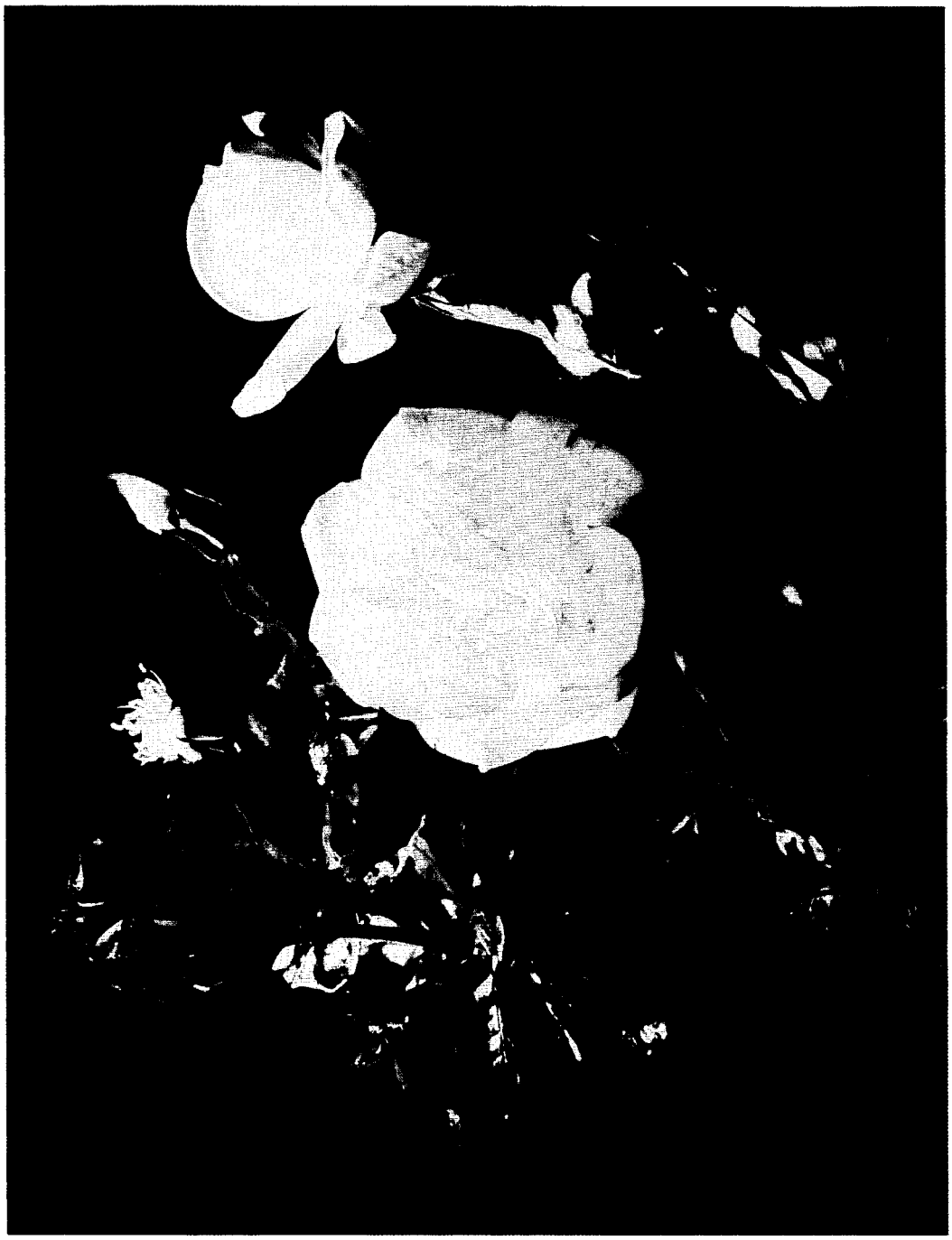
Inventor.
Marie Louise Meilland
By: Robb & Robb
Attorneys.

United States Patent Office

Plant Pat. 2,949
Patented Dec. 9, 1969

2,949
ROSE PLANT

Marie Louise Meilland, Cap d'Antibes, Alpes Maritimes, France

Filed Mar. 18, 1968, Ser. No. 714,133
Claims priority, application France, June 2, 1967, 48,742
Int. Cl. A01h *5/02*
U.S. Cl. Plt.—15 1 Claim

The present invention relates to a new and distinct variety of rose plant of the hybrid tea class, which was originated by me by crossing an unnamed and unpatented rose seedling of "Monte Carlo" (unpatented) × "Bettina" (unpatented) with an unnamed and unpatented rose seedling of "Peace" (U.S. Plant Patent No. 591) × "Soraya" (unpatended), the former being the seed parent and the latter being the pollen parent.

As the result of this breeding, I have produce a new and improved rose variety which is distinguished from its parents, as well as from all other rose varieties of which I am aware, as evidenced by the following unique combination of characteristics which are outstanding in the new variety:

(1) An exceptionally vigorous, freely branched, broad and upright habit of growth;

(2) Abundant, heavy and glossy foliage of Spinach Green color;

(3) A free and continuous blooming habit throughout the blooming season;

(4) A double flower form;

(5) Firm flower petals;

(6) A distinctive, attractive, pure yellow general color tonality of the flowers;

(7) Good color retention throughout the life of the flowers; and (8) A disease resistance comparable or superior to that of the average rose variety of its color class.

In comparison with its unnamed seed parent, the new variety has a more regular habit of growth, more abundant foliage, greater quantity of bloom, and a longer lasting flower quality when the flowers are cut.

As compared with its unnamed pollen parent, the new variety bears yellow flowers which hold their color well with little fading, whereas the flowers of this parent fade quickly.

Asexual reproduction of the new variety by budding, as performed in France and also at West Grove, Pa., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hard; bush; outdoor; seedling; for garden decoration.
Class: Hybrid tea.
Breeding: Seedling.
- *Seed parent.*—An unnamed seedling of "Monte Carlo" × "Bettina."
- *Pollen parent.*—An unnamed seedling of "Peace" × "Soraya."

Propagation: Holds its distinguishing characteristics through succeeding propagation by budding.

FLOWER

Locality where grown and observed: West Grove, Pa., U.S.A.
Flowers borne: Singly.
Quantity of bloom: Free, outdoors.
Continuity: Continuous.
Fragrance: Moderate. Nature—tea.
Bud:
- *Peduncle.*—Long; medium caliper; erect; almost smooth; with few red hairs. Color—light green.
- *Before calyx breaks.*—Size—medium large. Form—pointed; with small foliaceous appendages on the surface of the bud; with slender foliaceous parts extending beyond the tip of the bud equal to ½ or more of its length.
- *As calyx breaks.*—Color—Sulphur Yellow, Plate 1/1, with uneven flushes of Mars Orange, Plate 013/1 at petal edges.
- *As first petal opens.*—Size—medium. Form—medium length; pointed. Color: outside—Lemon Yellow, Plate 4/1, with slight shadings of Orange, Plate 12/2 at petal edges; inside—Lemon Yellow, Plate 4, deepening to Chinese Yellow, Plate 606 at petal edges; occasional petals may be striped with Canary Yellow, Plate 2/3.
- *Opening.*—Opens up well.

Bloom:
- *Size (when fully open).*—Medium large; from 3 inches to 4 inches.
- *Petalage.*—Very double (many petals, usually with no stamens showing); from 35 to 45 petals; arranged regularly.
- *Form.*—High-centered at first and remaining high-centered; petals being at first tightly rolled outward, but later becoming loosely rooled outward at maturity.

Petals:
- *Texture.*—Thick.
- *Appearance.*—Inside—satiny. Outside—velvety.
- *Shape.*—Outer—obovate. Intermediate — obovate. Inner—obovate, with 1 notch.

This description of a newly opened flower was made from a rose grown outdoors during the month of August at West Grove, Pa., U.S.A.:

*Color.*—Outer petals: outside surface—Lemon Yellow, Plate 4/2; inside surface—Lemon Yellow, Plate 4/1. Intermediate petal: outside surface—Canary Yellow, Plate 2/2, with very slight edging of Yellow Orchre, Plate 07/3; inside surface—Canary Yellow, Plate 2/2, shading to Aureolin, Plate 3 at the petal base. Inner petal: outside surface—Aureolin, Plate 3/2, shading through Aureolin, Plate 3/1 to Aureolin, Plate 3 at petal base; inside surface—Aureolin, Plate 3/1, shading to Aureolin, Plate 3 at petal base.

This description was made from a rose that was open for three days outdoors during the month of August at West Grove, Pa., U.S.A.:

*Color.*—Outer petal: outside surface—Aureolin, Plate 3/1; inside surface—Lemon Yellow, Plate 4/1. Inner petal: outside surface—Mimosa Yellow, Plate 602/1, shading to Mimosa Yellow, Plate 602 at petal base; inside surface—Mimos Yellow, Plate 602/1, shading to Mimosa Yellow, Plate 602, at petal base.

*General color effect.*—Newly opened flower—Aureolin, Plate 3, with occasional light markings of Mars Orange, Plate 013/1 and/or Canary Yellow, Plate 2/2. Three-days open—Aureolin, Plate 3/1, fading to Aureolin, Plate 3/2.

*Behavior.*—Drop off cleanly.

*Flower longevity.*—On bush in garden—5 days in August. Cut roses grown outdoors and kept at living-room temperatures—3 days in August.

REPRODUCTIVE ORGANS

Stamens: Many; regularly arranged about pistils; occasionally mixed with petaloids.

Filaments: Many; long; most with anthers. Color—Yellow Ochre, Plate 07/2.

Anthers: Medium large; all open at once. Color—Chrome Yellow, Plate 605.

Pollen: Moderate quantity. Color—gold.

Pistils: Medium number.

Styles: Uneven; medium length; medium caliper; bunched; columnar.

Stigma: Color—white and red.

Ovaries: All enclosed in receptacle.

Hips: None observed.

Sepals: Permanent; moderately long; spear-shaped; curled.

Seeds: None observed.

PLANT

Foliage:

*Leaves.*—Compound of 5 leaflets; very abundant; moderately large; very glossy.

*Leaflets.*—Shape—oval, with apex acute. Base—obtuse. Margin—simply serrate.

*Color.*—Mature: upper surface—Spinach Green, Plate 0960; undersurface—Lavender Green, Plate 000761/2, with some reddening at margins. Young: upper surface—Fern Green, Plate 0862, with Maroon; under surface—Maroon, Plate 1030/3.

*Rachis (the supporting stem of the compound leaf)*—Medium caliper. Upper side — smooth; grooved. Under side—smooth.

*Stipules.*—Moderately long; moderately narrow; with long points turning out at an angle of less than 45°; with glandular tipped hairs.

*Disease resistance.*—Comparable to that of the average rose variety grown under the same cultural conditions at West Grove, Pa., U.S.A.

Growth:

*Habit.*—Bushy; much-branched.

*Growth.*—Very free.

*Canes.*—Medium heavy.

*Main stems.*—Bright. Color—Scheele's Green, Plate 860/1. Prickles—several; color—Fern Green, Plate 0862/3. Hairs—none.

*Branches.*—Bright. Color—Scheele's Green, Plate 860/3. Prickles—few; color—lighter than Fern Green, Plate 0862/3. Hairs—none.

*New shoots.*—Bright. Color—Scheele's Green, Plate 860/3. Prickles—few; color—Scheele's Green, Plate 860/3. Hairs—none.

I claim:

1. A new and distinct variety of rose plant of the hybrid tea class, substantially as herein shown and described, characterized particularly as to novelty by the unique combination of an exceptionally vigorous, freely branched, broad and upright habit of growth, abundant, heavy and glossy foliage of Spinach Green color, a free and continuous blooming habit throughout the blooming season, a double flower form, firm flower petals, a distinctive, attractive, pure yellow general color tonality of the flowers, good color retention throughout the life of the flowers, and a disease resistance comparable or superior to that of the average rose variety of its color class.

No references cited.

ROBERT E. BAGWILL, Primary Examiner